(12) United States Patent
Negre

(10) Patent No.: US 10,357,639 B2
(45) Date of Patent: Jul. 23, 2019

(54) ADJUSTABLE DRAINAGE VALVE

(71) Applicant: SOPHYSA, Orsay (FR)

(72) Inventor: Philippe Negre, Paris (FR)

(73) Assignee: SOPHYSA, Orsay (FR)

( * ) Notice: Subject to any disclaimer, the term of this patent is extended or adjusted under 35 U.S.C. 154(b) by 471 days.

(21) Appl. No.: 15/022,260

(22) PCT Filed: Sep. 12, 2014

(86) PCT No.: PCT/IB2014/064476
§ 371 (c)(1),
(2) Date: Mar. 16, 2016

(87) PCT Pub. No.: WO2015/036976
PCT Pub. Date: Mar. 19, 2015

(65) Prior Publication Data
US 2016/0220794 A1    Aug. 4, 2016

(30) Foreign Application Priority Data

Sep. 16, 2013 (FR) ..................... 13 58897

(51) Int. Cl.
*A61M 27/00* (2006.01)
*A61M 39/24* (2006.01)

(52) U.S. Cl.
CPC .......... *A61M 27/006* (2013.01); *A61M 39/24* (2013.01); *A61M 2039/242* (2013.01);
(Continued)

(58) Field of Classification Search
CPC .... A61M 2039/242; A61M 2039/2433; A61M 2205/3515; A61M 27/006; A61M 39/24; A61M 2205/0272; A61M 2039/2493
See application file for complete search history.

(56) References Cited

U.S. PATENT DOCUMENTS 4,443,214 A    4/1984 Marion
5,167,615 A * 12/1992 East ................... A61M 27/006
                                                        137/854

(Continued)

FOREIGN PATENT DOCUMENTS

EP    0060369 A1    9/1982
EP    0688575 A1    12/1995
(Continued)

OTHER PUBLICATIONS

Jan. 30, 2015 Search Report issued in International Patent Application No. PCT/IB2014/064476.
(Continued)

*Primary Examiner* — Leslie R Deak
(74) *Attorney, Agent, or Firm* — Oliff PLC

(57) ABSTRACT

A drainage valve intended to be implanted and to drain the cerebrospinal fluid, including: a body defining a chamber into which there open an inlet port and an outlet port, a stopper capable of at least partially, or indeed completely, closing off the inlet port, a resilient return member exerting a resilient push force on the stopper towards the inlet port in order to open or close the port, a rotor housed in the chamber, able to rotate about an X-axis pivot and including a cam track on which the resilient return member rests such that the force exerted by the resilient return member on the stopper is modified by the rotation of the rotor.

21 Claims, 10 Drawing Sheets

(52) U.S. Cl.
CPC ............... *A61M 2039/2433* (2013.01); *A61M 2039/2493* (2013.01); *A61M 2205/0272* (2013.01); *A61M 2205/3515* (2013.01)

(56) References Cited

U.S. PATENT DOCUMENTS

| | | | |
|---|---|---|---|
| 5,637,083 | A | 6/1997 | Bertrand et al. |
| 5,643,194 | A | 7/1997 | Negre |
| 7,422,566 | B2 | 9/2008 | Miethke |
| 7,758,536 | B2 | 7/2010 | Cabaud et al. |
| 8,322,365 | B2 | 12/2012 | Wilson et al. |
| 2005/0010159 | A1 | 1/2005 | Reich et al. |
| 2007/0093741 | A1 | 4/2007 | Miethke |

FOREIGN PATENT DOCUMENTS

| | | | |
|---|---|---|---|
| EP | 0688575 | B1 | 9/1999 |
| EP | 1386634 | A1 | 2/2004 |
| EP | 1512428 | A1 | 3/2005 |
| EP | 1738792 | A1 | 1/2007 |
| EP | 2008683 | A1 | 12/2008 |
| EP | 1604703 | B1 | 8/2011 |
| EP | 2420284 | A2 | 2/2012 |
| WO | 02/47754 | A1 | 6/2002 |
| WO | 2006/091581 | A1 | 8/2006 |

OTHER PUBLICATIONS

Jan. 30, 2015 Written Opinion issued in International Patent Application No. PCT/IB2014/064476.

Takahashi, Yoshio. "Withdrawal of Shunt Systems—Clinical Use of the Programmable Shunt System and Its Effect on Hydrocephalus in Children". Child's Nerv Syst, Jun. 7, 2001, vol. 17, pp. 472-477.

Mariann Kordas et al. "Experience With SM8-300 Sophysa Adjustable Valve in Adult Chronic Hydrocephalus". Poster presented at Hydrocephalus Sep. 6-9, 2006, Gothenburg, Sweden.

* cited by examiner

SECTION A-A

SECTION B-B

ADJUSTABLE DRAINAGE VALVE

TECHNICAL FIELD

The subject of the present invention is a drainage valve intended for therapeutic applications, notably for the treatment of hydrocephalus which consists in shunting cerebrospinal fluid (CSF) contained in the ventricles of the cranial cavity toward a resorption site, for example the peritoneal cavity. The valve can be controlled from the outside in order, through the cutaneous tissues, to modify the passage or distribution of this fluid.

PRIOR ART

European patent EP 0 688 575 B1 discloses such a valve. It comprises a rotor to which a curved leaf spring is attached, the leaf spring pressing elastically against a ball in order to hold it against an inlet orifice of the valve so as to regulate the passage of fluid through this inlet orifice. The rotation of the rotor causes the point of contact of the ball on the leaf spring to slide, thereby altering the influence exerted by the leaf spring on the ball (corresponding to an opening pressure). The rotor may be locked/unlocked by mutual attraction and/or repulsion of micromagnets located on the rotor.

Also known, from European patent EP 1 604 703 or from American patents U.S. Pat. Nos. 7,422,566 B2 and 8,322,365 is a valve of which the rotor comprises a camway with a lateral or radial exterior profile, causing a translational movement perpendicular to the axis of rotation of the rotor. An elastic return member, attached to the body of the valve and pressing against the ball that shuts off the inlet orifice, also presses against the camway via mobile contact. In this configuration, the elastic return member exerts a pushing force comprising a centripetal component on the camway of the rotor. Rotation of the rotor thus makes it possible to modify the influence exerted by the elastic return member on the ball. Elsewhere, European patent applications EP 2 008 683 A1 and EP 1 738 792 A1 describe a valve of which the rotor has a helical or axial camway giving rise to a translational movement along the same axis as the axis of rotation of the rotor. This surface is in the form of "steps of a spiral staircase" against which there presses a first end of an elastic return member made up of a leaf spring mounted in the manner of a rocker between its two ends on the body of the valve. As previously, the elastic return member exerts a pushing force on the camway. Rotation of the rotor makes it possible to modify the height of the first end of the spring, and therefore the pressure of the other end of the spring on a shutter ball. A limited number of opening pressures is thus defined.

Applications US 2005/0010159 A1, WO 02/47754 A1, WO 2006/091581 A1 and EP 1 512 428 A1 describe still other examples of drainage valves for the treatment of hydrocephalus.

The valves need to be suited to the envisioned ranges of opening pressure: in particular, in certain cases of hydrocephalus, the neurosurgeon may need special pressures, outside of the standard range. In other cases, he will wish to have a wider choice of pressures within a determined range, which means to say of pressures separated by a smaller increment.

From as early as 1992, the Sophysa company has been manufacturing valves referred to as "special pressure range" valves capable of achieving high maximum opening pressures (SU8 200: from 80 to 200 mm $H_2O$), or even very high maximum opening pressures (SU8 300: of 50, 75, 95, 125, 150, 180, 220 and 300 mm $H_2O$, SU8 400: from 75 to 380 mm $H_2O$). The benefit to neurosurgeons of having a very high maximum opening pressure available lies in the possibility of temporarily halting the drainage of the cerebrospinal fluid through the valve thereby approximating as closely as possible a fully closed position (OFF position) thus testing the "shunt independency" of the patient, namely the patient's ability to tolerate the absence of a valve.

In 1995, Sophysa marketed a Sophy® Mini SM8 model covering a broadened standard pressure range from 30 to 200 mm $H_2O$ (30, 50, 70, 90, 110, 140, 170 and 200 mm $H_2O$) which in 1996 was extended to several special pressure range models capable of meeting almost all of the clinical requirements expressed by neurosurgeons: SM8-140 (10, 25, 40, 60, 80, 100, 120, 140 mm $H_2O$), SM8-300 (50, 75, 100, 125, 150, 180, 220, 300 mm $H_2O$) and SM8-400 (80, 120, 150, 190, 230, 270, 330, 400 mm $H_2O$). The SM8-400 model notably allowed Dr. Takahashi (Department of Pediatric Neurosurgery, Hokkaido Children's Hospital and Medical Center, Japan) to develop a severance technique in children that consisted in increasing the opening pressure in successive pressure levels until 400 mm $H_2O$ was reached, in maintaining this very high level for 6 to 24 months and in then removing the valve (Takahashi Y: "Withdrawal of shunt systems—Clinical use of the programmable shunt system and its effect on hydrocephalus in children". Child's Nerv Syst (2001) 17: 472-477). It was also demonstrated that the use of the SM8-300 model made it possible to reduce the complications of hyperdrainage during the postoperative period (Kordas M: "Experience with SM8-300 Sophysa adjustable valve in adult chronic hydrocephalus". Poster presented at Hydrocephalus 2006, 6-9 Sep., Gothenburg, Sweden). The SM8-140 model for its part allows patients afflicted with low-pressure hydrocephalus to be treated specifically.

Because on the one hand of the limited amplitude of the ranges of opening pressures available, and on the other hand of the limitation on the number of opening pressures available with a given model, notably in the range of high opening pressures, there is, however, today no valve that allows treatment of all types of hydrocephalus. The neurosurgeon has therefore to select the model of valve as a function of the etiology of each patient and the envisioned treatment strategy. Thus, if an error is made in diagnosing the etiology of the hydrocephalus or if the condition of the patient evolves in an unforeseen manner, the neurosurgeon may have to explant the valve and replace it with another model, offering a different range of opening pressures or offering a different number of positions.

It is one object of the present invention to propose a valve that is adjustable over a very broad range of opening pressures so as to allow neurosurgeons to treat all types of hydrocephalus using one single model of valve and do so whatever the therapeutic strategy adopted.

SUMMARY OF THE INVENTION

One subject of the invention is therefore a drainage valve intended to be implanted under the skin of a patient and to drain cerebrospinal fluid, said valve comprising:
- a body defining a chamber into which there open an inlet orifice and an outlet orifice for the cerebrospinal fluid,
- a shutter, preferably a ball, able to shut off the inlet orifice, at least partially, or even fully,
- an elastic return member designed to exert an influence on the shutter so as to push it, elastically, toward the inlet orifice so as to shut off said inlet orifice, the minimum pressure that allows the shutter to be moved in order to uncover the inlet orifice being referred to as the "opening pressure", a rotor housed in the chamber, able to rotate about an axis X between two extreme positions and comprising a camway against which the elastic return member bears so that the influence exerted by the elastic return member on the shutter is modified by the rotation of the rotor.

According to a first main aspect of the invention, the camway is defined by an interior profile, oriented toward the axis X, so that the elastic return member exerts a force, referred to as a "pulling force", comprising a component that is centrifugal with respect to the axis X, preferably a substantially centrifugal force, on the camway.

Said pulling force evolves in inverse proportion to the distance separating the axis X from the point of contact of the elastic return member with the camway. Thus, as this point of contact gets closer to the axis X, the pulling force and, therefore, the opening pressure resulting from the influence exerted by the elastic member on the shutter become higher, becoming smaller as the point of contact moves away from the axis.

Furthermore, for the same angular rotation of the rotor, the length of camway traveled by the point of contact of the elastic return member increases with greater distance of the point of contact away from the axis X and becomes shorter as this point of contact nears the axis. The successive angular positions corresponding to points of contact away from the axis X are therefore separated from one another by a longer length of camway than those corresponding to points of contact near the axis X. They may therefore be defined with greater mechanical precision, giving better precision to the corresponding opening pressures. Unlike the existing configurations in which the cam has an exterior profile which, for a point of contact distant from the center of the rotor, afford maximum precision in the high opening pressures, the design in which the cam has an interior profile affords maximum precision at the low opening pressures. This design is therefore better suited to the physiological needs of the patients as it affords high precision in the low pressures, where a 10 mm $H_2O$ difference in pressure may have a significant effect on the clinical condition of the patient, as in certain cases of normal pressure hydrocephalus or low pressure hydrocephalus, and lower precision in the very high pressures, where a variation of a few tens of mm $H_2O$ has only a limited impact on the clinical condition of the patient. As will be seen in more detail later on in the description, the camway may thus advantageously be very extensive about the axis X of the rotor. The setting of the influence exerted by the elastic return member on the shutter, namely the setting of the opening pressure, may therefore be very precise and/or the range of opening pressures may be very broad.

A valve according to the invention may also notably have one or more of the following optional features, in any possible combination:

the camway extends over more than 270°, over more than 300°, more than 320°, more than 340°, more than 350°, more than 355°, preferably over more than 370°, more than 540°, or even more than 720°, or more than 1080° about the axis X of rotation of the rotor; in one embodiment, the camway extends over 360°;

the camway is designed to provide first and second end stops for the elastic return member preventing the rotor from rotating beyond first and second extreme positions, in the first and second directions of rotation of the rotor, respectively;

the camway has no break in slope (or singular point), preferably extends in a spiral about the axis X, the gradient notably being able to be substantially constant;

the elastic return member is mounted to rotate, with respect to the body, about an axis Y substantially parallel to the axis X and comprises a lever arm in mobile contact with the camway and a bearing arm pressing against the shutter, the lever and bearing arms being connected to one another by a pivot passing through the axis Y, preferably substantially parallel to the axis X;

the lever arm defines, with the bearing arm, a sector of angle α intersecting the axis X whatever the position of the rotor, the direction of the lever arm being defined, when the valve is observed along the axis X, by the straight line passing through the axis Y and by the point at which the lever arm bears against the camway, and the direction of the bearing arm being defined, when the valve is observed along the axis X, by the straight line passing through the axis Y and the point at which the bearing arm presses against the shutter;

the elastic return member comprises either a rigid lever arm and a flexible bearing arm, preferably in the form of a leaf spring, preferably curved, or a flexible lever arm, preferably in the form of a flexible rod, and a rigid bearing arm, preferably in the form of a rigid leaf, preferably curved;

the lever arm is in mobile contact with the camway and comprises a rigid or flexible rod, preferably which is able to move and/or deform in a plane perpendicular to the axis X, preferably distinct from and preferably parallel to a plane perpendicular to the axis X and passing through the camway, and a cam follower, preferably substantially axial, in mobile contact with the camway;

the elastic return member exerts said pulling force for all angular positions of said rotor; in other words, the pulling force comprises a component diverging from the axis X along the entire length of the camway;

the camway is defined by a cavity formed in the rotor, particularly defined by a slot, a groove or a recess, or by a raised run of material;

the elastic return member and the rotor are configured to allow a valve opening pressure to be set in a range of an amplitude preferably greater than 150 mmH$_2$O, preferably greater than 200 mmH$_2$O, greater than 300 mmH$_2$O, greater than 350 mmH$_2$, greater than 400 mmH$_2$O, or even greater than 500 mmH$_2$O, or even greater than 600 mmH$_2$O;

the rotor may be positioned, preferably locked, in a plurality of predetermined angular indexing positions;

over at least one range of opening pressures, preferably over all of the opening pressures, the difference in opening pressure between two successive angular indexing positions, or "increment" is constant or variable, the increment evolving preferably substantially exponentially as the rotor rotates;

the rotor may be locked in twenty-four predetermined angular positions separated from one another by 15°, a rotation of the rotor in the clockwise direction, when looking at the external face of the rotor, leading to an increase in the opening pressure;

the rotor comprises a magnetic dipole formed of two micromagnets that are fixed or linearly mobile with respect to the rotor in a direction substantially radial with respect to the axis X and able to collaborate with rotor locking means so as to lock said rotor in a plurality of predetermined angular indexing positions. The angular indexing position, observed along the axis X, is defined by the angle β formed by the intersection of the straight line that passes through the axis X and the North pole of the magnetic dipole, with the straight line passing through the axis of the two, inlet and outlet, orifices;

the positions of the rotor evolve continuously and the gradient of the opening pressure as a function of the angular position of the rotor is constant or variable over at least one range of opening pressures, preferably over all the opening pressures, said gradient evolving preferably substantially exponentially as the rotor rotates;

the camway is configured to define several ranges of opening pressures, the opening pressure evolving differently according to which range of opening pressures is considered, it being possible for the increment or gradient notably to be constant in several ranges of opening pressures, and in particular in successive ranges;

for preference, the increment or the gradient increase from one range to the next, preferably such that the opening pressure increases substantially exponentially as the rotor rotates;

the axis of rotation of the rotor is off-centered with respect to the center of the chamber in which the rotor is housed and/or with respect to the axis connecting the cerebrospinal fluid inlet and outlet orifices.

The features described hereinabove may be combined with one another or with one or more of the features below.

According to a second main aspect of the invention, the camway of the rotor extends over 360°, preferably over more than 360°, more than 3700 or more than 400°, more than 720°, or even more than 1080° about the axis of the rotor.

According to a third main aspect of the invention, the elastic return member comprises a cam follower which is linearly guided along the camway. In a determined angular position of the rotor, the cam follower of the elastic return member may therefore not be moved radially away from the camway. Such guidance may, in particular, be achieved using a slot.

According to a fourth main aspect of the invention, the camway is configured so that the opening pressure does not vary in proportion with the angular position of the rotor. For preference, the opening pressure evolves more rapidly than the angular position of the rotor. In other words, starting from an angular position corresponding to a determined opening pressure, a determined angular movement of the rotor, for example by 15°, produces a variation in opening pressure that is higher the higher the initial opening pressure, preferably an exponential variation.

Unless there are technical incompatibilities, a feature of a valve according to one main aspect of the invention may be applied to a valve according to another main aspect of the invention.

A further subject of the invention is an implantable drainage device intended for draining or shunting cerebrospinal fluid of a patient and comprising:
 a valve according to the invention,
 a command unit able to transmit and/or receive instructions for modifying the angular position of the rotor about the axis X.

A further subject of the invention is a drainage or shunt assembly comprising:
 an implantable drainage device according to the invention,
 a control unit outside of the body of a patient and able to communicate with said command unit after the drainage device has been implanted in said body, preferably by a radiofrequency connection, notably to transmit and/or receive instructions and/or power.

The invention finally relates to the use of a drainage valve or shunt, to an implantable drainage device or drainage assembly according to the invention to drain cerebrospinal fluid.

DEFINITIONS

By definition, an opening pressure corresponds, in one position of the rotor, to the minimum pressure needed in order to move the shutter against the action of the influence exerted by the elastic return member on the shutter.

"Comprising a" or "including a" should be understood as meaning "comprising at least one" unless mentioned otherwise.

BRIEF DESCRIPTION OF THE FIGURES

The invention may be better understood from reading the nonlimiting detailed description thereof that follows and from studying the attached drawing, in which.

Figure 1:
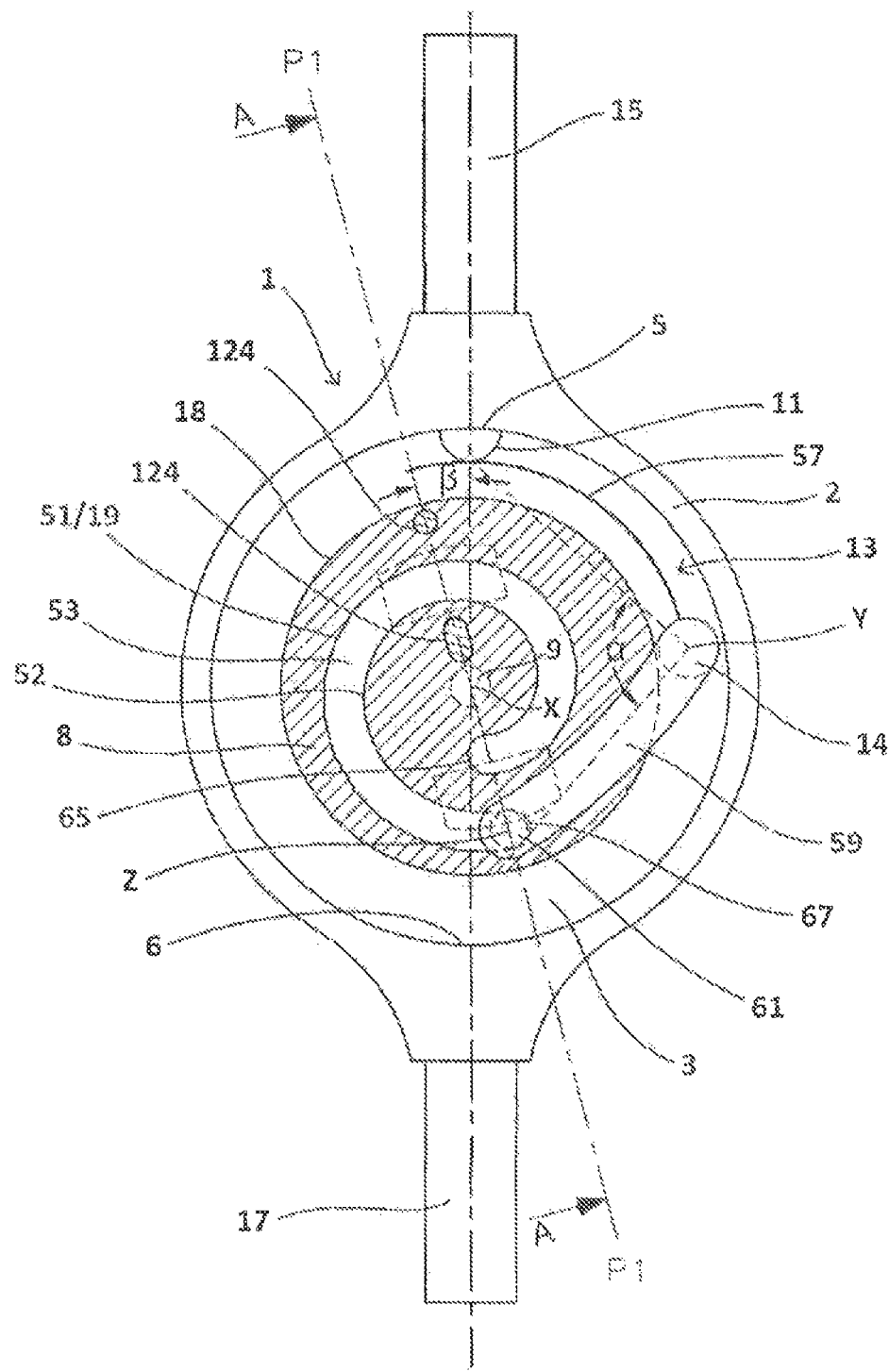
FIG. 1 schematically depicts a drainage valve according to the invention, in a position corresponding to a minimum opening pressure, observed along the axis X by the observer $O_a$, through the internal face of the body 2, FIG. 2 schematically depicts the valve of FIG. 1 in section on A-A in the plane $P_1$ depicted in FIG. 1, FIG. 3 schematically depicts the valve of FIGS. 1 and 2, observed along the axis X, through the external face of the body 2, by the observer $O_b$, with the exception of the radiopaque graduated dial 122 and the radiopaque indicator 124 of the rotor, FIG. 3a schematically depicts the valve of FIGS. 1 and 2, observed along the axis X, through the external face of the body 2, by the observer $O_b$ with the exception of the notches 117 of the central part 119.
Figure 2:
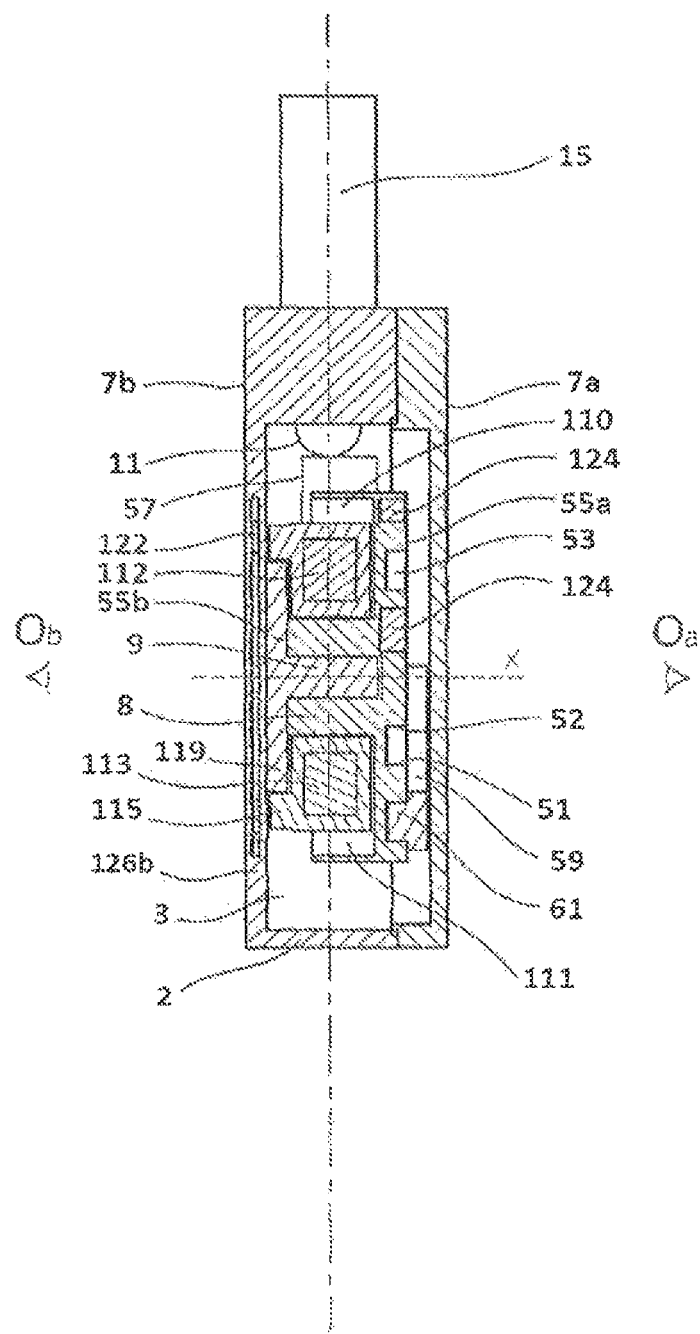

In the various figures, identical references have been used to denote members that are identical or similar.

DETAILED DESCRIPTION

The figures depict drainage valves 1 according to the invention, each comprising a body 2 defining a chamber 3 into which inlet 5 and outlet 6 orifices open. The chamber 3 is preferably substantially symmetrical, in particular with respect to the axis connecting the inlet 5 and outlet 6 orifices. For preference, it is substantially cylindrical of axis X.

The body 2 comprises an internal 7a and an external 7b face which faces are intended, after the device has been implanted under the skin of a patient, to be oriented toward the inside and the outside of the body of the patient, respectively.

A rotor 8, mounted with the ability to rotate about a pivot 9 of axis X of the body, a shutter consisting of a ball 11 and an elastic return member 13 pressing elastically against the ball 11 to hold it against the inlet orifice 5, are housed in the chamber 3.

An inlet pipe 15 and an outlet pipe 17 are fixed to the body 2 and open respectively via the inlet 5 and outlet 6 orifices. The inlet pipe 15 and the outlet pipe 17 may be respectively connected to a catheter bringing fluid and a catheter removing fluid, neither of which catheters have been depicted.

The rotor 8 comprises an exterior lateral surface 18, defining its thickness, extending substantially parallel to the axis X.

The exterior lateral surface of the rotor may be of any shape.

In one embodiment, the contour of the exterior lateral surface of the rotor 8 is substantially circular (observed along the axis X of rotation of the rotor) so that the distance between this surface and the bearing point at which the elastic return member presses on the shutter is substantially constant whatever the angular position of the rotor. The radial size of the valve is thereby reduced.

For preference, the rotor 8 is fixed with respect to the body along the axis X of rotation of the rotor. For preference, the body is substantially unable to be deformed by manual pressure (without a tool, using the strength in the hands alone).

The camway 19 is defined by all the points of contact between the rotor and the elastic return member during the greatest possible rotation of the rotor.

The distance between the bearing point at which the elastic return member presses on the camway and the axis of rotation of the rotor varies as a function of the angular position of said rotor, thereby making it possible to modify the force exerted by the elastic return member on the ball 11.

According to the invention, the camway is configured in such a way that the elastic return member exerts a force that has a centrifugal component, preferably a substantially centrifugal force, on the camway. The camway is thus defined by an interior profile of the rotor, oriented toward the axis X.

For preference, the elastic return member exerts a pulling force on the camway whatever the angular position of the rotor. In one embodiment, there is, however, a wide-open position in which the elastic return member exerts no pulling force on the camway, and therefore exerts no influence over the shutter.

The camway may in particular be a lateral or radial surface substantially parallel to the axis of rotation of the rotor.

For preference, the camway is configured so that contact with the elastic return member is permanent and continuous (with no "jump") as the rotor rotates. The compactness of the valve is thereby improved.

The shape of the camway is nonlimiting.

The camway may notably be defined by a hole in the rotor, which may or may not be a through-hole, particularly a slot (FIG. 1), a groove or a recess (FIG. 5) or by a raised run of material.

The camway may extend up to 360° about the axis of the rotor. For preference, the camway extends over more than 360° about the axis of the rotor.

The slope of the camway, which corresponds to the rate at which the opening pressure evolves per degree of rotation of the rotor, may be constant or increase as the rotor turns. The shape of the camway is suited to the desired rate of evolution of the opening pressure.

In one embodiment, the slope of the camway decreases, optionally in steps, as the rotor approaches its extreme angular position corresponding to a minimum opening pressure.

The valve according to the invention may or may not be provided with a motor (not depicted) to turn the rotor. In particular, the rotor may be driven by a magnetic dipole (fixed or mobile micromagnets) or by a stepping motor or even by a piezoelectric motor or, more generally, by any type of implantable micromotor.

In the absence of a motor, the rotor may be rotated manually, preferably by magnetically coupling the rotor to a magnet manipulated by the user.

Rotation of the rotor 8 makes it possible to modify the opening pressure.

The elastic return member 13 is preferably mounted so that it can rotate with respect to the valve body 2 about an axis Y preferably parallel to the axis X, preferably in the manner of a rocker, a first end of the elastic return member bearing against the shutter and a second end of the elastic return member bearing against the camway.

It may comprise a rigid or, preferably, elastic, bearing arm 57 pressing against the shutter, preferably curved so that it more or less runs alongside the exterior lateral surface 18 of the rotor, and an elastic or, preferably, rigid, lever arm 59 bearing against the camway, the pressure of the lever arm on the camway acting on the influence exerted by the bearing arm on the shutter. Of said bearing arm and said lever arm, at least one is rigid, the other being flexible.

The rigidity and elasticity of the bearing arm and of the lever arm are assessed with reference to their ability to be flexed in a plane perpendicular to the axis X of rotation of the rotor. The rigidity may, for example, be obtained by means of a rib or of a plate running substantially perpendicular to the axis X whereas flexibility may for example be obtained by using a blade running substantially parallel to the axis X of rotation of the rotor.

The bearing arm may comprise or consist of a leaf spring, preferably curved. A curved leaf spring advantageously confers a great deal of compactness. Under the effect of the tension resulting from the increase in opening pressure, the leaf spring may deform radially outward, in a plane perpendicular to the axis X. For preference, the lateral wall of the chamber in which the rotor is housed has an indentation making it possible to prevent the curved leaf spring from coming into contact with it as it deforms. In one embodiment, the axis of rotation of the rotor is offset with respect to the center of the chamber 3 and/or with respect to the axis connecting the inlet 5 and outlet 6 orifices.

The eccentricity or said offset is preferably greater than 0.3 mm, preferably greater than 0.5 mm, preferably greater than 0.8 mm, more preferably greater than or equal to 1 mm. Compactness is therefore optimized.

The lever arm may be made up of a rod extending preferably in a plane perpendicular to the axis X, able to pivot about the axis Y, and of a cam follower, preferably substantially axial, in mobile contact with the camway.

The cam follower is preferably formed of a pin 61, preferably a cylindrical pin, fixed to said rod, or of a roller, preferably mounted to rotate about an axis Z parallel to the axis X. The pin 61 preferably extends substantially parallel to the axis Y, preferably perpendicular to the lever arm 59, so that the elastic return member 13 straddles the rotor 8, preferably in all positions of the rotor 8. In other words, the elastic return member 13 has a shape that allows it to hook over the rotor 8 so as to come to bear against the interior profile (oriented toward the axis X).

The lever arm 59 extends, in the extension of the bearing arm 57, preferably forming with the bearing arm 57 an angle α preferably greater than 70°, greater than 80°, for the angular position of the rotor corresponding to the minimum opening pressure. The axis Y, defined by a pivot 14, passes through the junction of the bearing arm 57 with the lever arm 59.

The "open" configuration with the two arms of the elastic return member arranged one on each side of the axis X of rotation of the rotor, advantageously allows use to be made of a camway of long length and of an elastic return member, particularly a bearing arm, of long length. It is thus possible, in a small bulk, to set the opening pressure of the valve over a very broad range and/or with very good precision.

In the preferred embodiment, the bearing arm 57 is a curved leaf spring and the lever arm is rigid. In another embodiment, the bearing arm is a rigid blade and the lever arm is a flexible rod. The axis Y is preferably located as close as possible to, for example less than 2 mm away from, or less than 1 mm away from, the periphery of the rotor, preferably so that the bearing arm 57 extends, preferably facing the exterior lateral surface of the rotor, over an angular sector preferably of more than 70°. This configuration makes it possible to reduce the radial bulk of the valve body while at the same time optimizing the length of the two arms of the elastic return member. This optimization allows the range in which the opening pressures can be set to be extended considerably so that the one same valve can cover almost all of the currently desired ranges of opening pressures, namely an amplitude preferably equal to or greater than 400 mmH$_2$O, and makes it possible to allow fixed or variable increments between each position.

Figure 3:
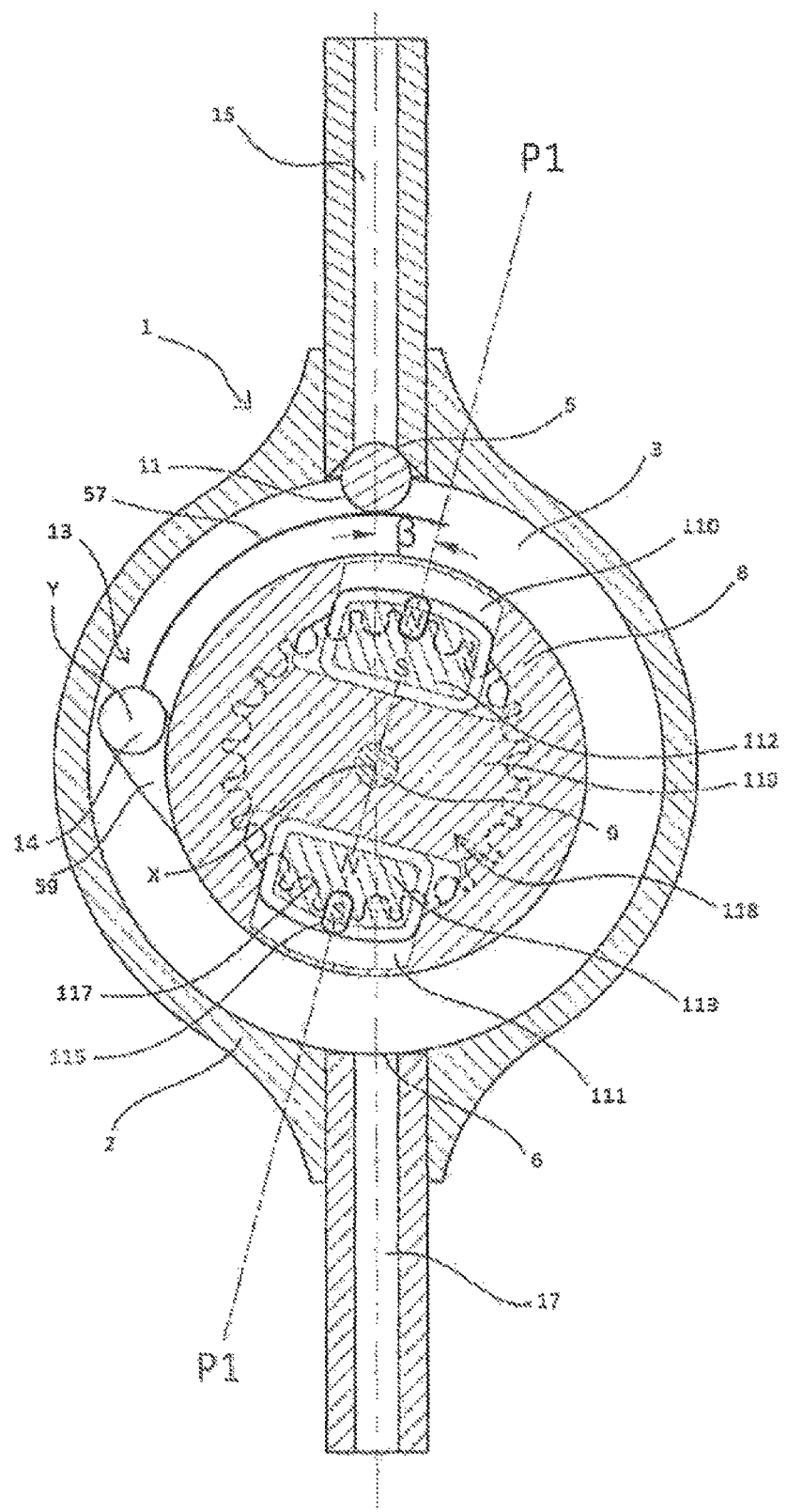
Figure 3A:
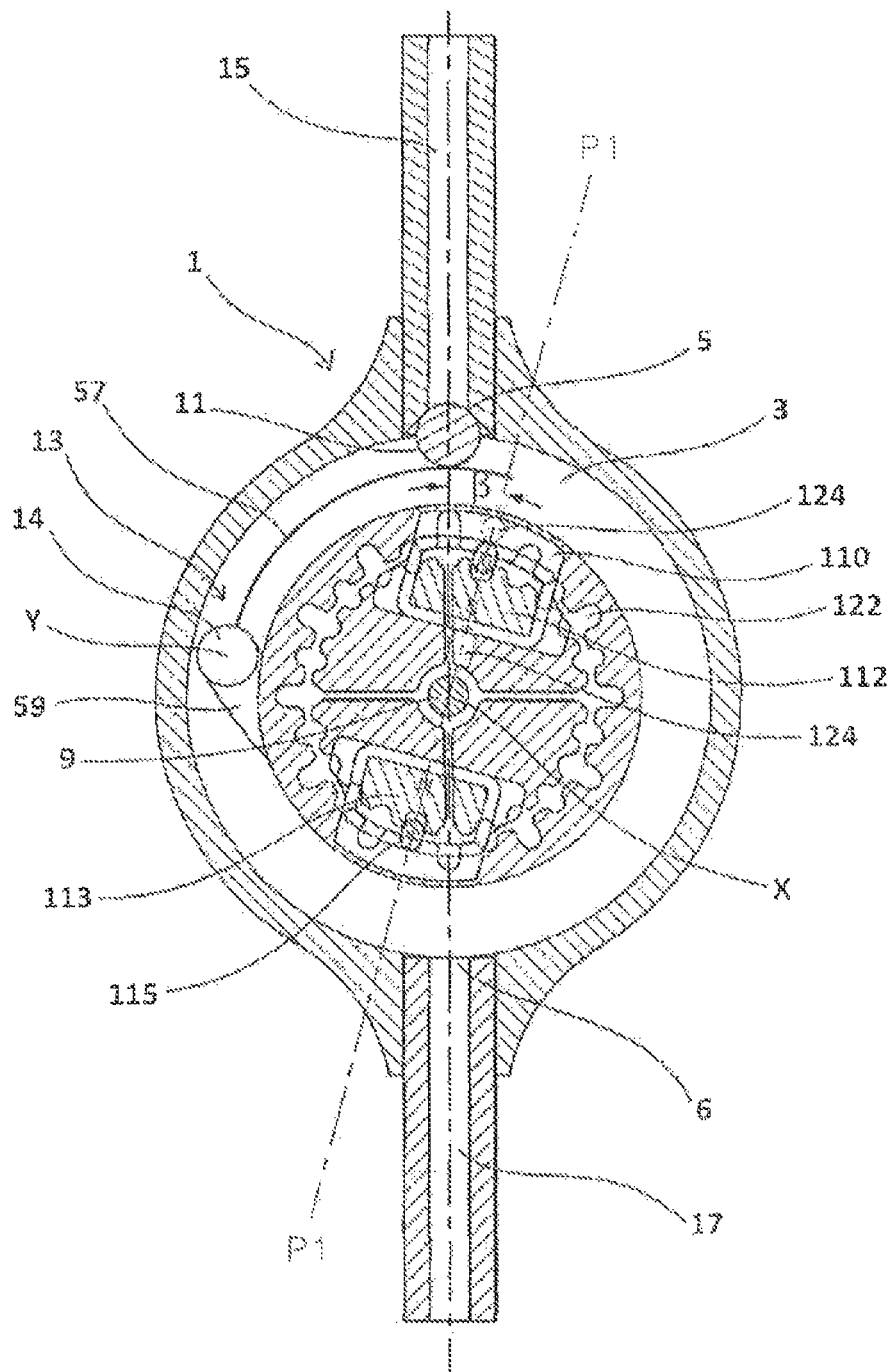
Figure 4:
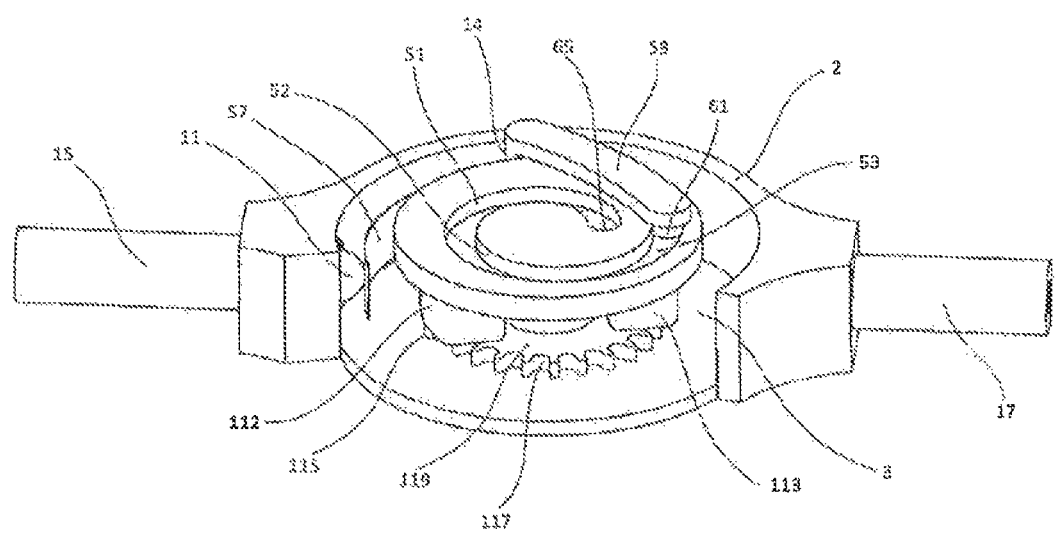
FIG. 4 is a schematic perspective depiction with cutaway of the valve of FIGS. 1, 2 and 3 with the exception of the radiopaque graduated dial 122 and of the radiopaque indicator 124 of the rotor, FIG. 5 schematically depicts, observed along the axis X by the observer $O_a$ (see FIG. 6) another embodiment of a valve according to the invention, in a position corresponding to a minimum opening pressure.

As depicted in FIGS. 3 and 4 in particular, the rotor preferably comprises at least one, preferably at least two, micromagnets 112 and 113, preferably two micromagnets able to move linearly with respect to the rotor in a direction that is substantially radial with respect to the axis X and which are able to collaborate with means of locking the rotor in a predetermined angular position.

The rotor may comprise one or several, particularly two, housings 110 and 111 each able to accommodate a micromagnet 112 and 113 respectively. Each micromagnet may be designed to be able to slide linearly in the corresponding housing in a substantially radial direction.

Each micromagnet may comprise a locking relief 115. This relief may for example comprise a cylindrical stud.

Each relief may be able to engage in a notch 117 of locking means 118.

The locking means may comprise a central part 119 that is fixed with respect to the body and on the periphery of which the notches are made. These notches may be uniformly distributed all around the axis of the rotor.

Using an external setting device it may be possible to move the micromagnets simultaneously in their respective housings, radially outward, so as to disengage the reliefs from the notches. This disengagement allows the rotor to be turned about the axis of rotation from one angular indexing position to another. The external setting device also allows the micromagnets to be positioned back in a locked position in which the reliefs are engaged in the notches.

Reference may be made to patent EP 1 604 703 B1, incorporated by reference, for further details regarding how the magnetic immobilization using the two micromagnets works and to patent EP 0 688 575 B1, incorporated by reference, for further details regarding the structure of the external setting device.

For preference, the rotor may adopt only a limited number of angular positions, referred to as "angular indexing positions". For preference, the angular separation between two angular indexing positions of the rotor is constant.

The difference in opening pressure corresponding to any two successive angular indexing positions, or "increment", is preferably less than 50 mmH$_2$O, 40 mmH$_2$O, 30 mmH$_2$O, 20 mmH$_2$O, 10 mmH$_2$O or even 5 mmH$_2$O.

Depending on the shape of the camway, it is possible to have different evolutions in increment and therefore to obtain different curves describing the variation in opening pressure as a function of the angular positions of the rotor.

In a first configuration, the opening pressures corresponding to each angular indexing position are separated by a fixed increment substantially equal to the range of opening pressures divided by the number of intervals between each position. For example, for a valve covering a 460 mmH$_2$O range of opening pressures, between 20 mmH$_2$O and 480 mmH$_2$O, with 24 indexing positions, and therefore 23 intervals, the increment will be 460/23=20 mmH$_2$O. The valve opening pressure therefore varies linearly as a function of the angular indexing position, whereas the percentage variation in opening pressure from one position to another, which is very high in the low-pressures range becomes particularly low in the high opening pressures range. Thus, simply passing from position 1 (20 mm) to position 2 (40 mm) represents a doubling of the resistance of the valve (+100%) which is liable to have an unfavorable impact on the clinical condition of certain patients. Conversely, moving from position 23 (460 mm) to position 24 (480 mm) represents a mere 4% increase, of which the impact on the clinical condition of the patient carries the risk of being relatively limited.

Table 1 illustrates this configuration:

TABLE 1

| Position | Pressure mmH$_2$O | Fixed increment mmH$_2$O | % variation |
|---|---|---|---|
| 1 | 20 | | |
| 2 | 40 | 20 | 100% |
| 3 | 60 | 20 | 50% |
| 4 | 80 | 20 | 33% |
| 5 | 100 | 20 | 25% |
| 6 | 120 | 20 | 20% |
| 7 | 140 | 20 | 17% |
| 8 | 160 | 20 | 14% |
| 9 | 180 | 20 | 13% |
| 10 | 200 | 20 | 11% |
| 11 | 220 | 20 | 10% |
| 12 | 240 | 20 | 9% |
| 13 | 260 | 20 | 8% |
| 14 | 280 | 20 | 8% |
| 15 | 300 | 20 | 7% |
| 16 | 320 | 20 | 7% |
| 17 | 340 | 20 | 6% |
| 18 | 360 | 20 | 6% |
| 19 | 380 | 20 | 6% |
| 20 | 400 | 20 | 5% |
| 21 | 420 | 20 | 5% |
| 22 | 440 | 20 | 5% |

TABLE 1-continued

| Position | Pressure mmH$_2$O | Fixed increment mmH$_2$O | % variation |
|---|---|---|---|
| 23 | 460 | 20 | 5% |
| 24 | 480 | 20 | 4% |

In a second configuration, rotation of the rotor from one angular indexing position to the next preferably leads, for each change in angular indexing position that tends to increase the opening pressure, to an increase in opening pressure which is higher the higher the opening pressure to which the initial angular indexing position corresponds.

In order to best meet the physiological needs of the patients, it is indeed preferable to have an increment the value of which is a function of the opening pressure or range of opening pressures concerned, so as to minimize the percentage variation in the low opening pressures ranges and maximize it in the high opening pressures ranges. Advantageously, the user may thus with better precision set the opening pressure when the opening pressure is not very high ("low pressure"), namely specifically in the range of opening pressures for which a variation in opening pressure has the greatest impact on the patient. Such a valve is therefore far better suited to the physiology of the patient than the valves of the prior art.

The following two evolutions in increment are preferred:

In a first preferred variable increment configuration the increment varies progressively throughout the range of pressures, preferably increasing with opening pressure so that the opening pressure varies substantially exponentially as a function of the angular indexing position. For example, the increment may vary progressively from 5 to 41 mm over a 400 mmH$_2$O range extending from 20 mm to 420 mmH$_2$O. The increase in opening pressure between position 1 (20 mm) and position 2 (25 mm) is just 25% here, whereas the increase in opening pressure between position 23 (379 mm) and position 24 (420 mm) is brought to 10.8%. A valve according to the invention therefore allows great precision in the low opening pressures.

Table 2 illustrates this configuration:

TABLE 2

| Position | Pressure mmH$_2$O | Progressive increment mmH$_2$O | % variation |
|---|---|---|---|
| 1 | 20 | | |
| 2 | 25 | 5.0 | 25.0% |
| 3 | 31 | 5.5 | 22.0% |
| 4 | 37 | 6.1 | 19.8% |
| 5 | 43 | 6.7 | 18.2% |
| 6 | 51 | 7.3 | 17.0% |
| 7 | 59 | 8.1 | 16.0% |
| 8 | 67 | 8.9 | 15.1% |
| 9 | 77 | 9.8 | 14.5% |
| 10 | 88 | 10.7 | 13.9% |
| 11 | 100 | 11.8 | 13.4% |
| 12 | 113 | 13.0 | 13.0% |
| 13 | 127 | 14.3 | 12.7% |
| 14 | 143 | 15.8 | 12.4% |
| 15 | 160 | 17.3 | 12.1% |
| 16 | 179 | 19.1 | 11.9% |
| 17 | 200 | 21.0 | 11.7% |
| 18 | 223 | 23.1 | 11.5% |
| 19 | 249 | 25.4 | 11.4% |
| 20 | 277 | 28.0 | 11.2% |
| 21 | 308 | 30.8 | 11.1% |
| 22 | 341 | 33.9 | 11.0% |

TABLE 2-continued

| Position | Pressure mmH$_2$O | Progressive increment mmH$_2$O | % variation |
|---|---|---|---|
| 23 | 379 | 37.3 | 10.9% |
| 24 | 420 | 41.0 | 10.8% |

In a second preferred variable increment configuration the increment is fixed for a given range of opening pressures but varies in steps from one range of opening pressures to another, preferably so that the opening pressure varies with an exponential trend as a function of the angular indexing position. Although not as well optimized as the preceding configuration in terms of variations in opening pressure, this stepwise configuration does on the other hand allow the practitioner easily to remember the increments and opening pressures of the valve. For example, the increments may be 10, 20 and 30 mm in 3 ranges of increasing opening pressures (from 20 to 120 mm, from 120 to 300 mm and from 300 to 420 mm respectively) or the increments may be increments of 10, 15, 20, 25 and 30 mm in 5 ranges of increasing opening pressures (from 20 to 100 mm, from 100 to 175 mm, from 175 to 255 mm, from 255 to 330 mm and from 330 to 420 mm respectively). In these two examples illustrating this second configuration, the increase in opening pressure may, between position 1 (20 mm) and position 2 (30 mm), be 50%, whereas the increase in opening pressure may, between position 23 (390 mm) and position 24 (420 mm), be 8%.

Tables 3 and 4 illustrate this configuration:

TABLE 3

| Position | Pressure mmH$_2$O | Stepped increment mmH$_2$O | % variation |
|---|---|---|---|
| 1 | 20 | | |
| 2 | 30 | 10 | 50% |
| 3 | 40 | 10 | 33% |
| 4 | 50 | 10 | 25% |
| 5 | 60 | 10 | 20% |
| 6 | 70 | 10 | 17% |
| 7 | 80 | 10 | 14% |
| 8 | 90 | 10 | 13% |
| 9 | 100 | 10 | 11% |
| 10 | 110 | 10 | 10% |
| 11 | 120 | 10 | 9% |
| 12 | 140 | 20 | 17% |
| 13 | 160 | 20 | 14% |
| 14 | 180 | 20 | 13% |
| 15 | 200 | 20 | 11% |
| 16 | 220 | 20 | 10% |
| 17 | 240 | 20 | 9% |
| 18 | 260 | 20 | 8% |
| 19 | 280 | 20 | 8% |
| 20 | 300 | 20 | 7% |
| 21 | 330 | 30 | 10% |
| 22 | 360 | 30 | 9% |
| 23 | 390 | 30 | 8% |
| 24 | 420 | 30 | 8% |

TABLE 4

| Position | Pressure mmH$_2$O | Stepped increment mmH$_2$O | % variation |
|---|---|---|---|
| 1 | 20 | | |
| 2 | 30 | 10 | 50% |

TABLE 4-continued

| Position | Pressure mmH₂O | Stepped increment mmH₂O | % variation |
|---|---|---|---|
| 3 | 40 | 10 | 33% |
| 4 | 50 | 10 | 25% |
| 5 | 60 | 10 | 20% |
| 6 | 70 | 10 | 17% |
| 7 | 80 | 10 | 14% |
| 8 | 90 | 10 | 13% |
| 9 | 100 | 10 | 11% |
| 10 | 115 | 15 | 15% |
| 11 | 130 | 15 | 13% |
| 12 | 145 | 15 | 12% |
| 13 | 160 | 15 | 10% |
| 14 | 175 | 15 | 9% |
| 15 | 195 | 20 | 11% |
| 16 | 215 | 20 | 10% |
| 17 | 235 | 20 | 9% |
| 18 | 255 | 20 | 9% |
| 19 | 280 | 25 | 10% |
| 20 | 305 | 25 | 9% |
| 21 | 330 | 25 | 8% |
| 22 | 360 | 30 | 9% |
| 23 | 390 | 30 | 8% |
| 24 | 420 | 30 | 8% |

For preference, the rotor may be indexed and/or locked in predetermined angular positions, these positions being distributed over an angular sector which may range up to 360°.

The number of angular indexing positions is preferably greater than or equal to 5, greater than 10, or even greater than 20 and/or less than or equal to 50, preferably less than 40, less than 30, 24 being considered to be an optimum number of positions.

For preference, the locking means 118 comprise 24 notches 117 uniformly distributed over 360° all about the axis X, giving an angle of 15° between notches, so that the rotor may be indexed and/or locked in 24 predetermined angular positions so as to cover an angular sector of 360°.

For preference, the 24 positions are arranged like the dial face of a "24-hour" clock, with opening pressures increasing in the clockwise direction and decreasing in the counterclockwise direction (when the valve is observed via its external face) so that position 1, corresponding to the lowest opening pressure, is situated at 1 o'clock and position 24, corresponding to the highest opening pressure, is situated in the 24-hours position (the 12 o'clock position of a normal clock).

The valves depicted in the figures comprise such a dial, FIGS. 8 to 11 corresponding to positions 1, 6, 12 and 24 respectively. For preference, the valve comprises a radiopaque graduated dial 122 fixed to the body, particularly a graduated wheel, preferably made of metal, preferably with 24 divisions, making it possible, in collaboration with a radiopaque indicator 124 of the rotor, for each angular indexing position, and therefore corresponding opening pressure, to be read easily by radiography. The graduated dial may in particular be made of a material based on tantalum or on titanium.

For preference, the graduations of the dial and the indicator consist of lines or studs or pins extending preferably substantially radially. For easier reading, the graduations are thickened preferably every 6, preferably every 2 divisions.

For preference, the graduated dial is a substantially flat component preferably fixed, facing the rotor 8, on the external wall 126b of the body 2 which defines the external face 7b, preferably without projecting. In particular, the body may be made of a synthetic material, for example plastic, and the graduated dial, for example in the form of a graduated wheel, may be housed in a cutout formed on the external wall 126b for that purpose.

The graduations that define the indexing positions may all be identical. In one embodiment, one or several graduations may be different than the others, for example so as to identify the position corresponding to the maximum opening pressure.

In one embodiment, the indicator of the rotor may extend, along a radius of the rotor, preferably so as to remain at least partially visible whatever the angular position of the rotor, and in particular when this position corresponds to a partial superposition of the lever arm with said indicator. This feature is particularly advantageous when the lever arm has the form of a plate extending substantially perpendicular to the axis X, as depicted in the figures.

When the rotor comprises a magnetic dipole formed of two micromagnets, the indicator is preferably situated at the North pole end.

In one embodiment, the positions of the rotor may evolve continuously (no indexing). The evolution in opening pressure may be substantially proportional to the evolution in the angular position of the rotor, which means to say that the gradient of the opening pressure as a function of the angular position of the rotor may be substantially constant. The opening pressure may thus evolve linearly as the rotor rotates. The opening pressure may notably evolve so that it corresponds, in the positions corresponding to those of Table 1, to the pressures mentioned in that table (fixed increment).

The gradient of the opening pressure as a function of the angular position of the rotor may also evolve, and preferably increase, preferably exponentially, with the opening pressure.

In other words, for the same amplitude of rotor rotation, the opening pressure may evolve more rapidly if the initial opening pressure is high. The opening pressure may notably evolve so as to correspond, in the positions corresponding to those of Table 2, to the pressures mentioned in that table.

The gradient may also be constant for a given range of opening pressures and vary in steps from one range of opening pressures to another, preferably so that the opening pressure varies with an overall exponential trend. The opening pressure may notably evolve so that it corresponds, in the positions corresponding to those of Tables 3 and 4, to the pressures mentioned in these tables.

Reference is now made to FIGS. 1 to 4.

The rotor defines a slot 53 preferably extending in a spiral about the axis X, preferably formed in the internal wall 55a of the rotor 8, which extends substantially perpendicular to the axis X. It is possible to make out the interior profile 51 and exterior profile 52 of the slot 53, which are oriented toward the inside (toward the axis X) and toward the outside, respectively.

The slot 53 may advantageously extend over more than 270°, more than 300°, more than 300°, more than 350°, even over more than 360°, or more than 370°, more than 720° or more than 1080° about the axis X of rotation of the rotor 8. For preference, the camway thus extends over more than 270°, more than 300°, more than 320°, more than 350°, or even over more than 360°, or more than 370°, or more than 400°, more than 720°, or even more than 1080° about the axis of the rotor. The setting precision is thereby improved and/or the breadth of the setting range is thereby increased.

The range for setting the opening pressure of the valve may thus notably extend over more than 300 mmH₂O, more than 400 mmH₂O, more than 450 mmH₂O or even more than 500 mmH₂O, more than 550 mmH₂O or even more than 600 mmH$_2$O. It may for example extend from 10 mmH$_2$O to over 500 mmH$_2$O.

The elastic return member 13 comprises an elastic bearing arm 57 and a lever arm 59 that is guided, via the pin 61, by pressing against the interior profile defined by the lateral surface of the slot (mobile contact), guidance of the lever arm 59 acting on the influence exerted by the bearing arm 57 on the ball 11.

The cam follower, in this instance a pin 61 mounted to slide in the guide slot 53, is in permanent contact with the interior profile 51 of the slot, which thus defines the camway 19.

The pin 61 may thus exert a substantially centrifugal action on the surface of the slot.

In the conventional way, for the very low opening pressures, the pressure of the elastic return member on the rotor, and therefore the pressure of the elastic return member on the shutter, may be momentarily interrupted, for example in the event of a knock. Advantageously, a slot provides guidance that prevents any lateral shifting of the cam follower, thus ensuring that it can move only along the slot. Thus, the guiding afforded by the slot exerts an action that ensures that the elastic return member bears constantly against the shutter. This guidance is of particular benefit when the elastic return member, and particularly the lever arm, is very long.

The ends 65 and 67 of the slot constitute end stops for the pin 61, preventing the rotor from rotating beyond the extreme HP and LP positions corresponding to the highest and lowest opening pressures respectively. They also prevent any "jump" in pressure between these two extreme positions.

Figure 5:
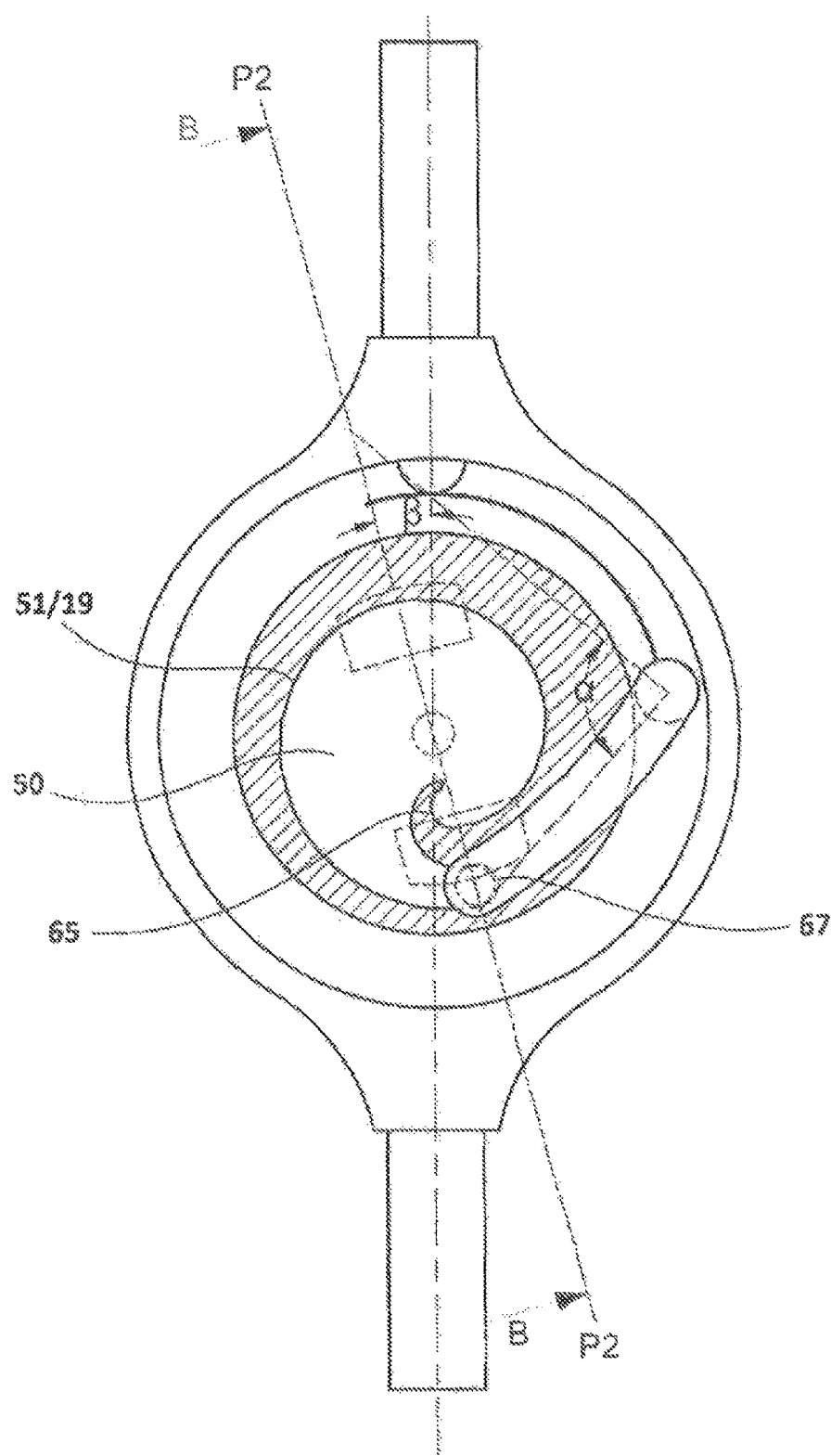
Figure 6:
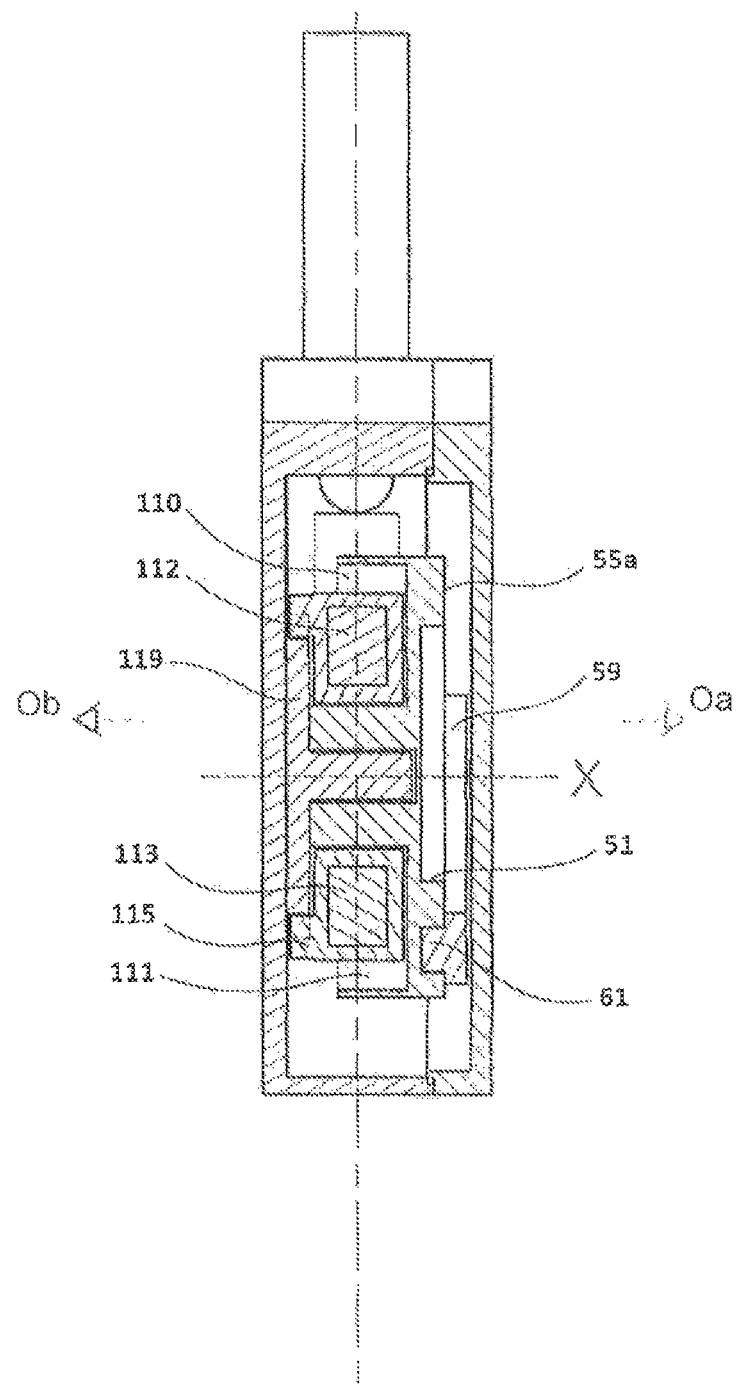
FIG. 6 is a schematic depiction in section on B-B in the plane $P_2$ (see FIG. 5) of the valve depicted in FIG. 5.
Figure 7:
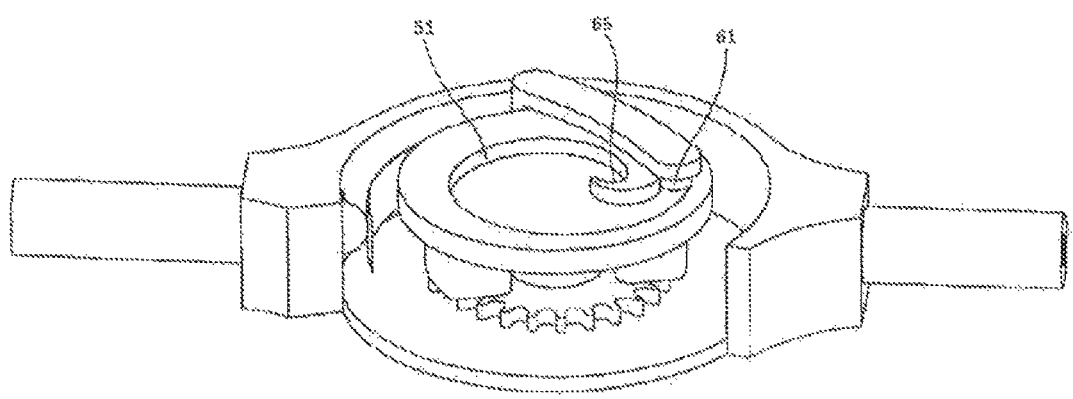
FIG. 7 is a schematic perspective depiction with cutaway of the valve depicted in FIGS. 5 and 6, FIGS. 8, 9, 10 and 11 depict the valve of FIG. 7 in angular positions of the rotor which, on a 24-position dial, correspond to positions 1, 6, 12 and 24, (the suffixes a and b correspond to what is seen by observers $O_a$ and $O_b$ respectively, namely via the internal and external faces of the body, respectively.
Figure 8A:
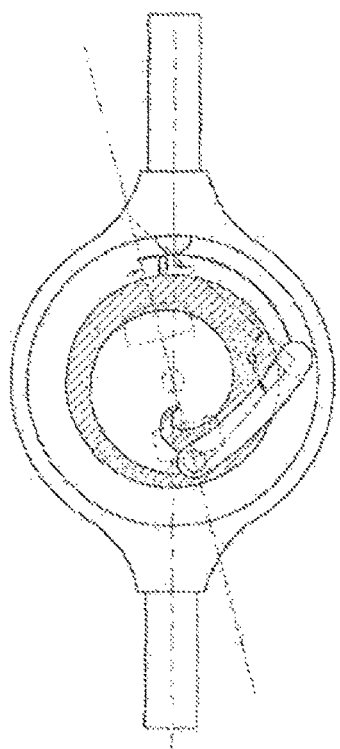
Figure 8B:
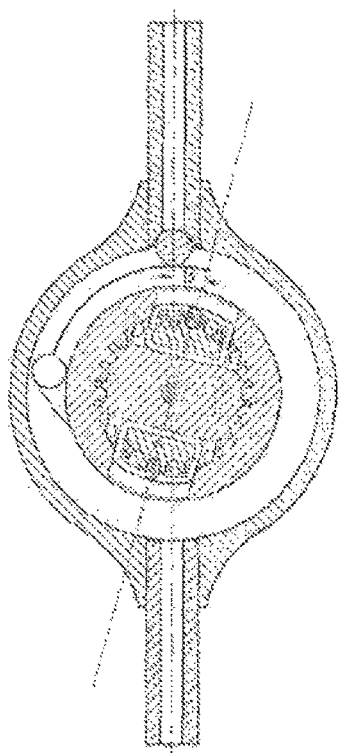
Figure 9A:
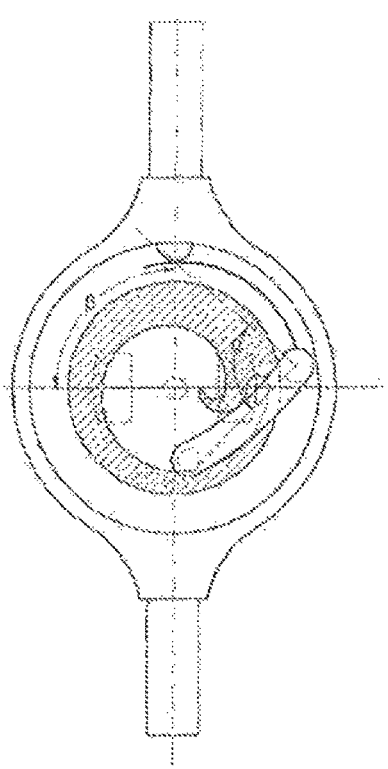
Figure 9B:
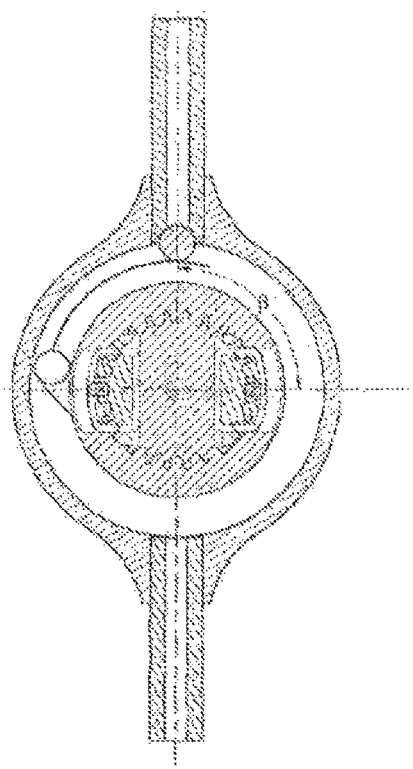
Figure 10A:
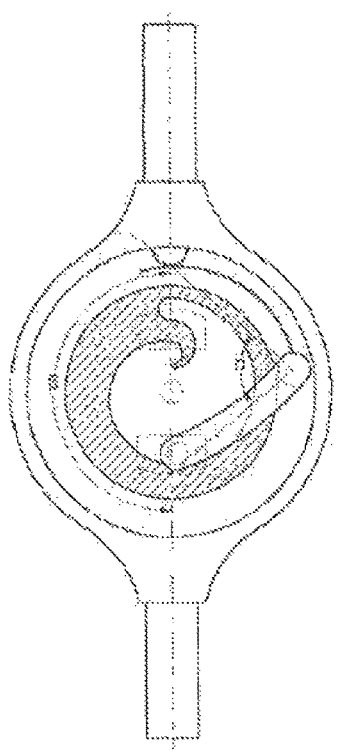
Figure 10B:
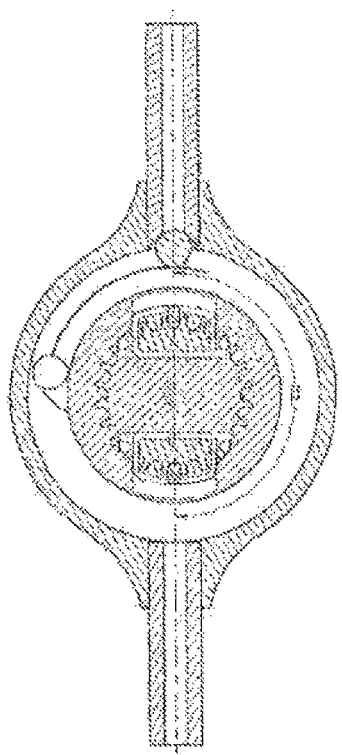
Figure 11A:
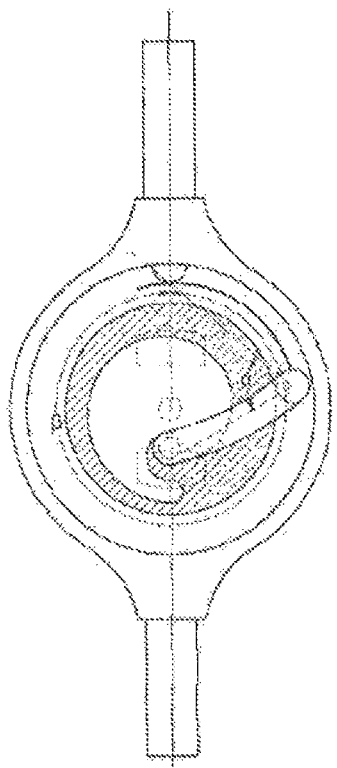
Figure 11B:
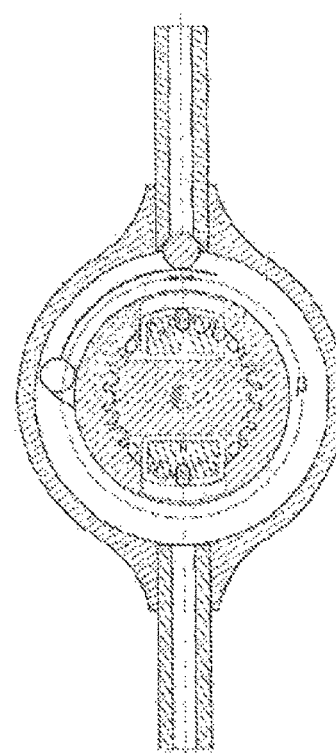

FIGS. 5 to 7 illustrate the possibility of having a camway that allows a centrifugal action on the elastic return member 13 by creating a recess 50, possibly a through-recess, in the internal 55a or external 55b wall (which walls are oriented toward the inside and toward the outside of the body of the patient, respectively) of the rotor 8, preferably in the internal wall 55a or, which is the equivalent, by providing a raised run of material there.

The camway 19 has a radius that decreases over an angular sector substantially equal to 360°, in the clockwise direction when the valve is observed from the internal face thereof.

Operation

After a valve 1 has been implanted in the body of a patient, the operator sets the angular position of the rotor.

To each angular position of the rotor 8 there corresponds an influence exerted by the bearing arm 57 on the ball 11. This influence, exerted elastically, corresponds to the minimum pressure needed for the cerebrospinal fluid upstream of the inlet orifice 5 to be able to clear the ball 11 at least partially away from the inlet orifice 5 and thus flow into the chamber 3. This pressure is referred to as the opening pressure.

The camway 19 is in the form of a spiral so that the angular position of the pin 61 about the axis Y is directly dependent on the angular position of the rotor 8 about the axis X. Rotation of the rotor 8 therefore leads to rotation of the lever arm 59 about the axis Y and, because the bearing arm 57 is fixed to the lever arm 59, to a variation in the influence exerted by the bearing arm 57 on the ball 11. The opening pressure is thus set by moving the pin 61 along the camway 19.

The camway and the elastic return member are arranged in such a way that a rotation of the rotor in the clockwise direction (with respect to the external face, i.e. the face that will be oriented toward the skin of the patient) has the effect of moving the lever arm 59 closer to the axis X of the rotor 8, closing up the angle α formed by the two arms of the elastic return member, the consequence of this being an increase in the influence exerted by the bearing arm 57 on the ball 11, an increase in the opening pressure of the valve and a reduction in the rate of flow of cerebrospinal fluid.

Conversely, a rotation of the rotor 8 in the counterclockwise direction has the effect of moving the lever arm further away from the axis X of the rotor thereby opening up the angle α formed by the two arms of the elastic return member, the consequence of this being a reduction in the influence exerted by the bearing arm 57 on the ball 11 and therefore a decrease in the opening pressure of the valve and therefore an increase in the rate of flow of cerebrospinal fluid.

The valve thus behaves in a way similar to that of a tap that the operator operates: he closes the tap by turning the rotor in the clockwise direction until it reaches the end stop of position 24 which corresponds to an almost closed position (the "virtual OFF" position at more than 400 mmH$_2$O). He opens the tap by turning the rotor in the counterclockwise direction until the end stop for position 1 corresponding to an almost wide open position (very low pressure) is reached.

The cerebrospinal fluid that has entered the chamber 3 passes to the outlet orifice 6 and is then discharged. When the quantity of fluid discharged is high enough, the pressure of cerebrospinal fluid upstream of the opening orifice 5 decreases until it drops below the opening pressure, leading the bearing arm 57 to push the ball 11 back onto its seat in order to shut off the inlet orifice 5 and thus halt the removal of cerebrospinal fluid.

If need be, the operator may easily modify the angular position of the rotor 8 and thus set the opening pressure.

As is now clearly evident, a valve 1 according to the present invention allows precise setting of the opening pressure, over a very broad range, particularly when the camway extends over more than 360°.

Of course, the invention is not limited to the exemplary embodiments just described.

The present invention may be adapted to suit any type of adjustable-pressure valve.

According to one advantageous embodiment, it is adapted to an adjustable valve with magnetic locking, as described in U.S. Pat. No. 5,643,194 or EP 0688 575 or patent EP 1 604 703 or U.S. Pat. No. 7,758,536.

The camway is not necessarily a through-way, like when it is defined by the slot 53 or the recess 50. In particular, the slot may be replaced by a groove.

The elastic return member may be of any type.

Having a camway that has a plurality of notches distributed, for example uniformly, about the axis X would not constitute a departure from the scope of the present invention.

These notches may be configured to correspond to angular indexing positions of the rotor.

The elastic return member may be configured to be able to engage in these notches.

It is also possible to envision a camway which extends only over an angular sector of less than 360°, for example over an angular sector of approximately 180°.

The evolutions in opening pressure described in the context of a valve comprising predetermined angular indexing positions may be applied to any type of valve and, in particular, to valves allowing a continuous evolution in the opening pressure. The slope of the camway may easily be adapted for that purpose.

The features of the various embodiments, particularly of the embodiments depicted, may be combined, unless they are technically incompatible.

REFERENCES FOR THE FIGURES

1: drainage valve
2: valve body
3: chamber
5: CSF inlet orifice
6: CSF outlet orifice
7a and 7b: internal and external faces of the body 2
8: rotor
9: rotor pivot
11: ball (shutter)
13: elastic return member
14: elastic return member pivot
15: inlet pipe
17: outlet pipe
18: exterior lateral surface of the rotor 8
19: camway
50: recess in the rotor
51: interior profile of the slot 53 or of the recess 50
52: exterior profile of the slot 53
53: slot
55a and 55b: internal and external walls of the rotor, respectively
57: bearing arm for pressing against the shutter
59: lever arm
61: pin (or stud) in contact with the cam surface
65 and 67: ends of the slot 53 or of the recess 50 defining end stops for high and low pressure
110 and 111: housings for the micromagnets
112 and 113: micromagnets
115: locking relief (stud)
117: notches
118: locking means
119: fixed central part supporting the notches
122: radiopaque graduated dial
124: radiopaque indicator of the rotor
126b: external wall of the body 2
X: axis of rotation of the rotor
Y: axis of pivoting of the elastic return member
α: angle formed between the two arms of the elastic return member

The invention claimed is:

1. A drainage valve intended to be implanted under the skin of a patient and to drain cerebrospinal fluid, said valve comprising:
a body defining a chamber into which there open an inlet orifice and an outlet orifice for the cerebrospinal fluid,
a shutter able to shut off the inlet orifice at least partially, or even fully,
an elastic return member designed to exert an influence on the shutter so as to push it, elastically, toward the inlet orifice so that the passage of cerebrospinal fluid through the inlet orifice is possible only if its pressure is greater than or equal to an opening pressure,
a rotor housed in the chamber, able to rotate about an axis X between two extreme positions and comprising a camway against which the elastic return member bears so that the influence exerted by the elastic return member on the shutter is modified by the rotation of the rotor,
the camway being defined by an interior profile of the rotor, directed toward the axis X, so that the elastic return member exerts, on the camway of the rotor, a force referred to as a "pulling force" comprising a component that is centrifugal with respect to the axis X.

2. The valve as claimed in claim 1, the camway extending over more than 320° about the axis X of rotation of the rotor.

3. The valve as claimed in claim 2, the camway extending over more than 370° about the axis X of rotation of the rotor.

4. The valve as claimed in claim 1, the camway being designed to provide first and second end stops for the elastic return member preventing the rotor from rotating beyond first and second extreme positions, in the first and second directions of rotation of the rotor, respectively.

5. The valve as claimed in claim 1, in which the camway has no break in slope, extends in a spiral about the axis X, and the gradient is substantially constant.

6. The valve as claimed in claim 1, in which the elastic return member is mounted to rotate, with respect to the body, about an axis Y substantially parallel to the axis X and comprises a lever arm in mobile contact with the camway and a bearing arm pressing against the shutter, the lever and bearing arms being connected to one another by a pivot passing through the axis Y,
the lever arm forming, with the bearing arm, a sector of angle intersecting the axis X,
the direction of the lever arm being defined, when the valve is observed along the axis X, by the straight line passing through the axis Y and by the point at which the lever arm bears against the camway, and
the direction of the bearing arm being defined, when the valve is observed along the axis X, by the straight line passing through the axis Y and the point at which the bearing arm presses against the shutter.

7. The valve as claimed in claim 6, in which the lever arm in mobile contact with the camway comprises a rigid or flexible rod, which is able to move and/or deform in a plane perpendicular to the axis X, distinct from and parallel to a plane perpendicular to the axis X and passing through the camway, and a substantially axial cam follower in mobile contact with the camway.

8. The valve as claimed in claim 1, in which said elastic return member exerts said pulling force for all angular positions of said rotor.

9. The valve as claimed in claim 1, the camway being defined by a cavity formed in the rotor, defined by a slot, a groove or a recess, or by a raised run of material.

10. The valve as claimed in claim 1, the elastic return member and the rotor being configured to allow a valve opening pressure to be set in a range of an amplitude greater than 200mmH$_2$O, or even greater than 350mmH$_2$.

11. The valve as claimed in claim 1, the rotor comprising a magnetic dipole formed of two micromagnets that are fixed or linearly mobile with respect to the rotor in a direction substantially radial with respect to the axis X and able to collaborate with rotor locking means so as to lock said rotor in a plurality of predetermined angular indexing positions.

12. The valve as claimed in claim 1, in which, in at least one range of opening pressures,
the rotor may be positioned in a plurality of predetermined angular indexing positions and the increment between two opening pressures corresponding to two successive angular positions of the rotor is constant.

13. The valve as claimed in claim 1, in which, in at least one range of opening pressures, the rotor may be positioned in a plurality of predetermined angular indexing positions and the increment between two opening pressures corresponding to two successive angular positions of the rotor is variable.

14. The valve as claimed in claim 13, in which said increment or said gradient evolves substantially exponentially as the rotor rotates.

15. The valve as claimed in claim 1, in which the camway is configured to define several ranges of opening pressures, the opening pressure evolving differently according to which range of opening pressures is considered.

16. The valve as claimed in claim 15, in which the rotor may be positioned in a plurality of predetermined angular indexing positions, the increment between two opening pressures corresponding to two successive angular indexing positions being constant in several ranges of successive angular positions of the rotor, the increment increasing, from one range to the next, and the positions of the rotor may evolve continuously and the gradient of opening pressure as a function of the angular position of the rotor is constant in several ranges of successive angular positions of the rotor, said gradient increasing, from one range to the next.

17. The valve as claimed in claim 1, in which the elastic return member comprises either a rigid lever arm and a flexible bearing arm, or a flexible lever arm and a rigid bearing arm.

18. The valve as claimed in claim 1, in which the rotor may be locked in twenty-four predetermined angular positions separated from one another by 15°, a rotation of the rotor in the clockwise direction, when looking at the external face of the rotor, leading to an increase in the opening pressure.

19. The valve as claimed in claim 1, in which the axis of rotation of the rotor is off-centered with respect to the center of the chamber in which the rotor is housed and/or with respect to the axis connecting the cerebrospinal fluid inlet and outlet orifices.

20. The valve as claimed in claim 1, in which, in at least one range of opening pressures, the positions of the rotor may evolve continuously and the gradient of opening pressure as a function of the angular position of the rotor is constant.

21. The valve as claimed in claim 1, in which, in at least one range of opening pressures, the positions of the rotor may evolve continuously and the gradient of the opening pressure as a function of the angular position of the rotor is variable.

* * * * *